United States Patent [19]

Mülhaupt et al.

[11] Patent Number: 4,874,805
[45] Date of Patent: Oct. 17, 1989

[54] NOVEL OXAZOLIDINES

[75] Inventors: Rolf Mülhaupt, Marly, Switzerland; Hubert Simon, Mulhouse, France

[73] Assignee: Ciba-Geigy Corporation, Ardsley, N.Y.

[21] Appl. No.: 212,853

[22] Filed: Jun. 29, 1988

Related U.S. Application Data

[62] Division of Ser. No. 70,741, Jul. 6, 1987, Pat. No. 4,772,716.

[30] Foreign Application Priority Data

Jul. 14, 1986 [CH] Switzerland ................ 2817/86

[51] Int. Cl.$^4$ ................................ C08K 5/54
[52] U.S. Cl. ............................ 524/188; 524/262; 524/265; 524/266; 524/267; 524/268; 524/719; 524/730
[58] Field of Search .............. 524/188, 262, 265, 266, 524/267, 268, 719, 730

[56] References Cited

U.S. PATENT DOCUMENTS

| | | | |
|---|---|---|---|
| 4,772,716 | 9/1988 | Mulhaupt et al. | 548/110 |
| 4,797,439 | 1/1989 | Peccoux | 524/188 |

*Primary Examiner*—Melvyn I. Marquis
*Attorney, Agent, or Firm*—Luther A. R. Hall

[57] ABSTRACT

Compounds of the general formula I

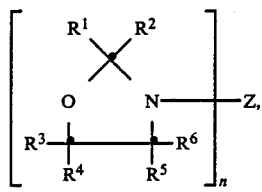

in which $R^1$ is hydrogen, $C_1$-$C_{12}$-alkyl, $C_5$-$C_7$-cycloalkyl, phenyl or benzyl and $R^2$ is hydrogen or $C_1$-$C_4$-alkyl, or $R^1$ and $R^2$, together with the C atom to which they are attached, form a 5-membered or 6-membered ring, and $R^3$, $R^4$, $R^5$ and $R^6$ are identical or different and are hydrogen, $C_1$-$C_{12}$-alkyl, phenyl which is unsubstituted or monosubstituted to trisubstituted by $C_1$-$C_4$-alkyl, halogen or $C_1$-$C_4$-alkoxy, or is a group of the formula —$CH_2OR^7$ (II) in which $R^7$ is $C_1$-$C_{12}$-alkyl, phenyl which is unsubstituted or monosubstituted to trisubstituted by $C_1$-$C_4$-alkyl, halogen or $C_1$-$C_4$-alkoxy, or is —C(O)—$R^8$, and $R^8$ is $C_1$-$C_{12}$-alkyl, and also not more than two of the radicals $R^3$, $R^4$, $R^5$ and $R^6$ are one or two groups of the formula —$CH_2CH_2Si(OR^9)_3$ (III), —$CH_2OC(O)CH_2Si(OR^9)_3$ (IV), —$Ch_2O(C_mH_{2m})Si(OR^9)_3$ (V) or

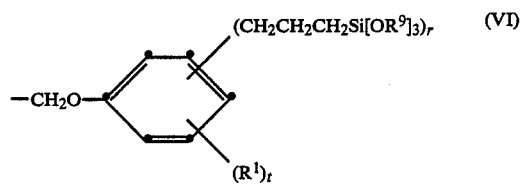

in which $R^9$ is $C_1$-$C_4$-alkyl or phenyl and m is a number from 1 to 8 and r is a number 1 or 2 and t is 0, 1, or 2 and $R^1$ is as defined above, and, in addition, compounds of the formula I in which $R^4$ and $R^5$ together from a group of the formula

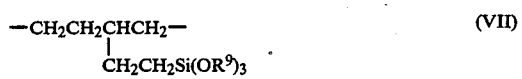

in which $R^9$ is as defined above and $R^3$ and $R^6$ in this case are hydrogen and n is 1 or 2 and, if n is 1, Z is an organic radical which is derived from a primary amine $ZNH_2$ and can contain one or two —$Si(OR^9)_3$ groups and, if n is 2, Z is a divalent organic radical derived from a diprimary diamine $H_2NZNH_2$; subject to the proviso that the compounds of the formula I contain one to three —$Si(OR^9)_3$ groups, are suitable for use as adhesion promoters, particularly for moisture-curing epoxide and polyurethane resins.

3 Claims, No Drawings

NOVEL OXAZOLIDINES

This is a divisional of application Ser. No. 070,741, filed on July 6, 1987, now U.S. Pat. No. 4,772,716, issued on Sept. 20, 1988.

The present invention relates to novel 1,3-oxazolidines containing silane groups, to their preparation and their use as adhesion promoters and to epoxide resins or polyurethane resins curing by means of moisture which contain these adhesion promoters and which can be employed as adhesives, sealing compositions, paints or insulating materials.

1,3-oxazolidines have been described, for example in U.S. Pat. Specification No. 3,743,626, as curing agents for polyurethane prepolymers which cure by moisture.

Prepolymers of this type have been known for a long time as adhesives, sealing materials, paints or insulating materials. The curing properties of these prepolymers are based on their content of free isocyanate groups, which results in curing under the influence of moisture. The adhesion of the cured polyurethane to glass or metal is unsatisfactory in many technical applications, which has led to the use of primers. A good bond between the polyurethane and glass or metal is achieved by this means, and this bond is not greatly impaired even by high humidity, elevated temperatures and high mechanical stress. Examples of primers which have proved suitable are aminoallkylalkoxysilanes (cf. Plueddemann et al. "Silane coupling agents", Plenum Press, NY [1982]). However, the most effective aminosilane adhesion promoters cannot be used in an unmodified form as adhesion promoters incorporated into moisture-curing polyurethanes, since the amino groups react with isocyanate groups. For this reason, ketimines and aldimines of aminoalkylsilanes which can be added to polyurethane adhesives without impairing their stability on storage have been described in German Offenlegungsschrift No. 3,414,877.

A class of compounds has now been found, which are added to moisture-curing polyurethane and epoxide resin adhesives, sealing materials, paints and insulating materials, whereby no gelling takes place and a significantly increased adhesion to glass, metal and plastics, such as glass fibre-reinforced plastics, is achieved. This adhesion is retained even after storage for several weeks in water at 60° C. In this method it is possible to dispense with the pretreatment with a primer, which means dispensing with a separate, additional operation. These results are surprising, since the addition to polyurethane of glycidyloxypropyltrimethoxysilane, which is used in nearly all resins, produces a markedly weaker adhesion.

The present invention relates to compounds of the general formula I

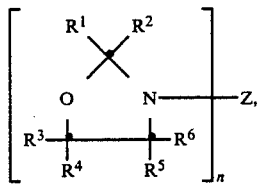

in which $R^1$ is hydrogen, $C_1$-$C_{12}$-alkyl, $C_5$-$C_7$-cycloalkyl, phenyl or benzyl and $R^2$ is hydrogen or $C_1$-$C_4$-alkyl, or $R^1$ and $R^2$, together with the C atom to which they are attached, form a 5-membered or 6-membered ring, and $R^3$, $R^4$, $R^5$ and $R^6$ are identical or different and are hydrogen, $C_1$-$C_{12}$-alkyl, phenyl which is unsubstituted or monosubstituted to trisubstituted by $C_1$-$C_4$-alkyl, halogen or $C_1$-$C_4$-alkoxy; or is a group of the formula —$CH_2OR^7$ (II) in which $R^7$ is $C_1$-$C_{12}$-alkyl, phenyl which is unsubstituted or monosubstituted to trisubstituted by $C_1$-$C_4$-alkyl, halogen or $C_1$-$C_4$-alkoxy, or is —C(O)—$R^8$, and $R^8$ is $C_1$-$C_{12}$-alkyl, and also not more than two, preferably one, of the radicals $R^3$, $R^4$, $R^5$ and $R^6$ are one or two groups of the formula —$CH_2CH_2Si(OR^9)_3$ (III), —$CH_2OC(O)CH_2$—$CH_2Si(OR^9)_3$ (IV), —$CH_2O(C_mH_{2m})Si(OR^9)_3$ (V) or

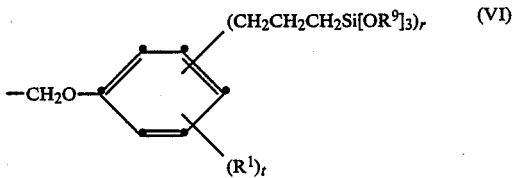

in which $R^9$ is $C_1$-$C_4$-alkyl or phenyl and m is a number from 1 to 8 and r is a number 1 or 2 and t is 0, 1 or 2 and $R^1$ is as defined above, and, in addition, compounds of the formula I in which $R^4$ and $R^5$ together form a group of the formula

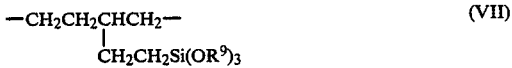

in which $R^9$ is as defined above and $R^3$ and $R^6$ in this case are hydrogen and n is 1 or 2 and, if n is 1, Z is an organic radical which is derived from a primary amine $ZNH_2$ and can contain one or two —$Si(OR^9)_3$ groups and, if n is 2, Z is a divalent organic radical derived from a primary diamine $H_2NZNH_2$; subject to the proviso that the compounds of the formula I contain one to three —$Si(OR^9)_3$ groups.

If $R^1$, $R^3$, $R^4$, $R^5$, $R^6$, $R^7$ and $R^8$ are $C_1$-$C_{12}$-alkyl, preferably $C_1$-$C_1$-alkyl, they are, for example, methyl, ethyl, n-propyl, isopropyl, n-butyl, isobutyl, t.-butyl, n-pentyl, n-hexyl or linear or branched octyl, nonyl, decyl, undecyl or dodecyl.

The preferred meaning of $R^3$, $R^4$, $R^5$ and $R^6$ as alkyl is methyl. Compounds of the formula I which are particularly preferred are those in which $R^3$, $R^4$, $R^5$ and $R^6$ are hydrogen or $C_1$-$C_4$-alkyl, and not more than two of these radicals are phenoxymethyl, and, in particular, those compounds in which $R^3$ and $R^6$ are hydrogen and $R^4$ and $R^5$ are methyl.

If the symbols $R^3$, $R^4$, $R^5$ and $R^6$ occur twice in compounds in which n is 2, these two radicals preferably have the same meaning in each case.

If $R^2$ and $R^9$ are $C_1$-$C_4$-alkyl, they can be, for example, methyl, ethyl, n-propyl, isopropyl, n-butyl, isobutyl or t.-butyl.

If $R^1$ is $C_5$-$C_7$-cycloalkyl, it is preferably cyclopentyl or cyclohexyl.

In preferred compounds, $R^1$ and $R^2$ independently of one another are hydrogen or $C_1$-$C_4$-alkyl, and, in particular, one of the radicals $R^1$ and $R^2$ is hydrogen and the other is $C_1$-$C_4$-alkyl.

If $R^3$, $R^4$, $R^5$, $R^6$ and $R^7$ are substituted phenyl, examples of suitable radicals are o-, m- or p-methylphenyl, 2,4-dimethylphenyl, 2,4,6-trimethylphenyl, p-ethylphenyl, p-t.-butylphenyl, 2-chlorophenyl or 4-methoxyphenyl.

If n is 1, the radical Z is derived from a primary amine. In accordance with the present invention, the meaning of Z in the primary amine $ZNH_2$ is of minor importance. It will be readily understood that those skilled in the art will select amines in which Z in the oxazolidine of the formula I does not react with the prepolymer in the absence of moisture, and the adhesion promoter according to the invention is therefore capable of forming mixtures with the propolymer which are stable on storage.

Preferred compounds are those of the formula I in which, if n is 1, Z is derived from an aliphatic, cycloaliphatic, aliphatic/aromatic, aromatic or heterocyclic primary amine, it being possible for this linear or branched radical Z to contain, if appropriate, one or more ester, ether, urethane, thiourethane, aldimine or ketimine groups.

Particularly preferred compounds are those of the formula I in which, if n is 1, Z is derived from an aliphatic or mixed aliphatic/aromatic primary amine, this radical Z containing, if appropriate, a total of one or two ester, ether, urethane, thiourethane, aldimine or ketimine groups, or being derived from an aromatic amine.

If the compounds of the formula I contain a radical Z which has one or more, preferably one or two and particularly preferably one, ester group, the ester group nearest to the oxazolidine ring is preferably attached to the oxazolidine nitrogen via alkyelene and the ester oxygen.

If Z in the compounds of the formula I contains ether oxygens, it can be a monoether or oligoether, for example a group of the formula $-(-CH[CH_3]-CH_2-O)_y$ or $-(-CH_2CH_2CH_2CH_2-O)_y$ in which y is a number from 1 to 20, preferably 1 to 8.

If carbamate or thiocarbamate groups are present in the radical Z in the compounds of the formula I, these compounds are derivatives whch can be obtained by reacting n-hydroxyalkyloxazolidines with compounds containing isocyanate or isothiocyanate groups. They are also to be understood as including radicals which contain both a urethane and a thiourethane group, for instance compounds which contain a bridge member of the formula

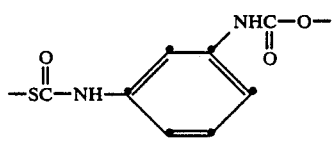

and the like.

If the radical Z in the compounds of the formula I contains aldimine or ketimine groups, these are, for instance, groups such as are described in German Offenlegungsschrift No. 3,414,877, for example the group $-N=C(CH_3)_2$. This category of substituents also includes, for example, a radical of the formula

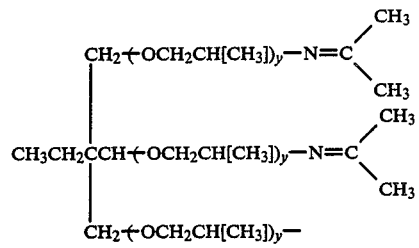

derived from a Jeffamin ®.

In preferred compounds of the formula I, the radical Z contans two ester, carbamate, thiocarbamate, aldimine or ketimine groups, in particularly preferred compounds it contains one ester, carbamate, thiocarbamate, aldimine or ketimine group. In this regard the ether groups constitute a certain exception, since they are capable, as has been pointed out above, of forming oligoether bridge members. Compounds of this type can therefore contain up to 20, preferably up to 8, ether groups. In the case of radicals having several independent oligoether bridge members, for example the Jeffamin ® derivative described above, compounds of this type can contain even more ether groups in the radical Z.

It is a characteristic essential to the invention that the compounds of the formula I should contain one to three $-Si(OR^9)_3$ groups. As defined above, if n is 1, the radical Z contains no silane groups or one or two silane groups, and, if n is 1, not more than two, preferably one, of the substituents $R^3$, $R^4$, $R^5$ and $R^6$ contains two, preferably one, silane group. In compounds of the formula I in which n is 2, no more than one or two of the radicals $R^3$, $R^4$, $R^5$ and $R^6$ present in total in the molecule are substituted by silane groups, symmetrical compounds being preferred-as mentioned above.

In compounds in which n is 2, Z as an organic radical is an aliphatic, cycloaliphatic or aromatic radical or a radical containing heteroatoms. Examples of these are the group $—C_vH_{2v}—$ in which v can be 1-20, 1,4-cyclohexylene, 1,4-phenylene, 1,3-phenylene or polyethers terminated by an amino group, and other radicals derived from a diprimary diamine $H_2NZNH_2$.

Compounds containing one or two silane groups are particularly preferred.

If a silane group is present in the radical Z, the compounds concerned are preferably compounds of the formula I in which Z is a group of the formula $-(-C_mH_{2m}-)Si(OR^9)_3$ (VIII), $-[(R^{10})C(R^{11})]_u-O-R^{12}$ (IX) or $-(R^{10})C(R^{11}) C(O)O(CH_2)_3Si(OR^9)_3$ (X) in which u is 2, 3 or 4 and $R^{10}$ and $R^{11}$ are hydrogen or methyl and $R^{12}$ is a group of the formula $-(-C_mH_{2m}-)Si(OR^9)_3,$ (XI)

$-C(O)CH_2CH_2Si(OR^9)_3,$ (XII)

$-C(O)NH-(-C_mH_{2m}-)Si(OR^9)_3,$ (XIII)

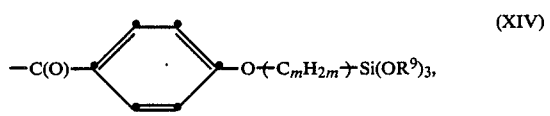 (XIV)

-continued $$-C(O)NH-\underset{NHC(O)S(C_mH_{2m})Si(OR^9)_3}{\underset{|}{\bigotimes}}(R^1)_t \quad \text{or} \quad (XV)$$

$$-C(O)NH-\underset{CH_2NHC(O)S(C_mH_{2m})Si(OR^9)_3}{\underset{|}{\bigodot}}{}^{(R^1)_t}_H \quad (XVI)$$

in which the symbols m, t, $R^1$ and $R^9$ are as defined above.

Compounds in which $R^{10}$ and $R^{11}$ are hydrogen are preferred in this respect.

u is 2, 3 or 4, 2 being preferred.

m is 1 to 8, preferably 2 to 4 and particularly preferably 3.

t is 0, 1 or 2, preferably 0 or 1.

If one or two, preferably one, silane group is present in not more than one of the radicals $R_3$, $R^4$, $R^5$ or $R^6$, preferred compounds of the formula I are those in which the silane group(s) is present in the substituent $R^3$ or $R^4$. Examples of such compounds contain substituents of the formulae (III), (IV), (V) or (VI), which have been defined above. In these compounds, m is 1 to 8, preferably 2 to 4 and particularly preferably 3. The preferred meaning of r is 1; the case where r is 2 provides a precise example of a compound in which two silane groups are present in not more than one of the substituents $R^3$, $R^4$, $R^5$ or $R^6$. t is preferably 0 or 1.

In compounds of this type, Z can, for example be a group of the formula XVII $$-[(R^{10})C(R^{11})]_{\overline{n}}OR^7$$

in which the symbols n, $R^7$, $R^{10}$ and $R^{11}$ are as defined above.

The following are examples of compounds of the formula I:

| n | $R^1$ | $R^2$ | $R^3$ | $R^6$ | Z |
|---|---|---|---|---|---|
| 1 | H | $\underset{-CH-CH_3}{\overset{CH_2}{\mid}}$ | $(CH_3O)_3Si(CH_2)_3OCH_2-$ | H | $-(CH_2)_3Si(OC_2H_5)_3$ |
| 1 | H | $\underset{-CH-CH_3}{\overset{CH_3}{\mid}}$ | —OCH$_2$— | H | $-(CH_2)_3Si(OC_2H_5)_3$ |
| 1 | $-CH_3$ | $-C_2H_5$ | 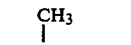—OCH$_2$— | H | $-(CH_2)_3Si(OC_2H_5)_3$ |
| 1 | H | $\underset{-CH-CH_3}{\overset{CH_3}{\mid}}$ | H | H | $-CH_2CH_2O\overset{O}{\overset{\|}{C}}NH(CH_2)_3Si(OC_2H_5)_3$ |
| 1 | H | $\underset{-CH-CH_3}{\overset{CH_3}{\mid}}$ | H | H | $-CH_2CH_2O\overset{O}{\overset{\|}{C}}NH-$ 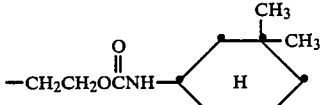 $-NHC(S)(CH_2)_3Si(OCH_3)_3$ with $CH_3$, $CH_3$, H substituents |
| 1 | $-CH_3$ | $-C_2H_5$ | $-CH_3$ | H | $-CH_2-\underset{CH_3}{\overset{\|}{CH}}O\overset{O}{\overset{\|}{C}}NH(CH_2)_3Si(OC_2H_5)_3$ |
| 1 | $-CH_3$ | $-C_2H_5$ | $(CH_3O)_3Si(CH_2)_3OCH_2-$ | H | $-(CH_2)_3CH_3$ |
| 1 | H | $\underset{-CH-CH_3}{\overset{CH_3}{\mid}}$ | $(CH_3O)_3Si(CH_2)_3OCH_2-$ | H | $-(CH_2)_4N=\!\!\!<\!\!\!\overset{H}{\underset{\underset{CH_3}{\overset{\|}{CH-CH_3}}}{}}$ |
| 1 | H | $\underset{-CH-CH_3}{\overset{CH_3}{\mid}}$ | H | H | $-CH_2\underset{CH_3}{\overset{\|}{CH}}-\overset{O}{\overset{\|}{C}}-O-(CH_2)_3Si(OCH_3)_3$ |
| 2 | $-CH_3$ | $-C_2H_5$ | $-CH_2O(CH_2)_3Si(OC_2H_5)_3$ | H | $-(CH_2)_6-$ |

-continued

| n | $R^1$ | $R^2$ | $R^3$ | $R^6$ | Z |
|---|---|---|---|---|---|
| 2 | H | $CH_3$<br>$-CH-CH_3$ | $-CH_2O(CH_2)_3Si(OC_2H_5)_3$ | H | $-(CH_2)_4O(CH_2)_4-$ |
| 2 | H | $CH_3$<br>$-CH-CH_3$ | $-CH_2O(CH_2)_3Si(OC_2H_5)_3$ | H | 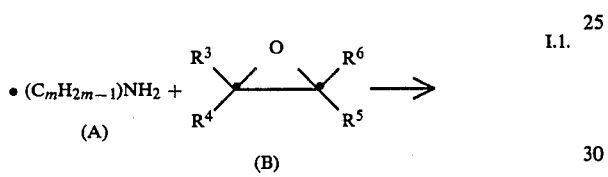 |
| 2 | H | $CH_3$<br>$-CH-CH_3$ | $-CH_2O(CH_2)_3Si(OC_2H_5)_3$ | H | 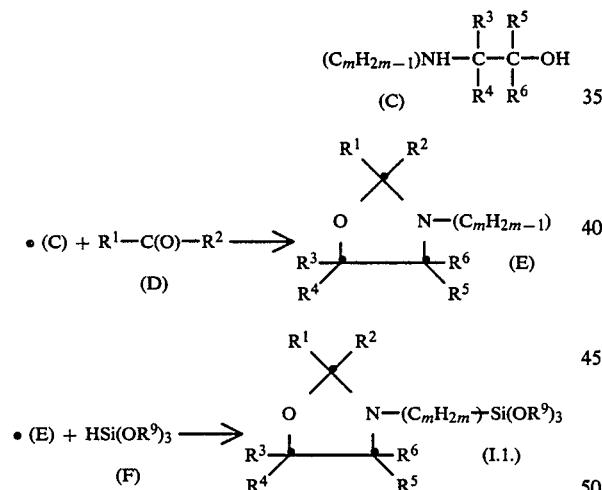 |

This refers to compounds in which $R^4$ and $R^5$ are hydrogen.

The preparation of the compounds of the formula I is effected in a manner known per se and can be illustrated most simply be means of the following reaction schemes:

I. Silane in Z, if n is 1:

● $(C_mH_{2m-1})NH_2$ + 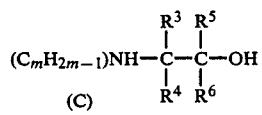 $\longrightarrow$  I.1.

(A)      (B)

$$(C_mH_{2m-1})NH-\underset{R^4}{\overset{R^3}{C}}-\underset{R^6}{\overset{R^5}{C}}-OH$$
(C)

● (C) + $R^1-C(O)-R^2 \longrightarrow$ 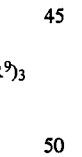 (E)
(D)

● (E) + $HSi(OR^9)_3 \longrightarrow$ (I.1.)
(F)

The first two stages can be carried out, for example, analogously to the methods described in EP-A 96,768, i.e. a primary alkenylamine (A), preferably containing vinyl groups, is reacted with an approximately equimolar amount of a monoepoxide compound (B) at approximately 60°–130° C. It is preferable to carry out the reaction of the epoxide and the amine in ethanol in the presence of catalytic amounts of an acid, for example p-toluenesulfonic acid.

The introduction of the silane group carried out in the third stage is a known addition reaction, which can be carried out in the presence of platinum catalysts, for example $H_2PtCl_6$, or in the presence of a peroxide.

The staring materials (A), (B), (D) and (F) employed in this method are known compounds; they are in part commercially available or can be prepared in a known manner. The reactive thinners customary in epoxide resin chemistry are preferably employed as the epoxide component.

● $(R^9O)_3Si+C_mH_{2m})NH_2$ + (B) $\longrightarrow$  I.2.

(G)

$$(R^9O)_3Si+C_mH_{2m})NH-\underset{R^4}{\overset{R^3}{C}}-\underset{R^6}{\overset{R^5}{C}}-OH$$
(H)

● (H) + (D) $\longrightarrow$ (I.1.)

This method is carried out analogously to the methods described in EP-A 96,768. The educts (B), (D) and (G) are known compounds, in some cases commercially available or they can be prepared in a simple known manner.

● $HN+\underset{R^4}{\overset{R^3}{C}}-\underset{R^6}{\overset{R^5}{C}}OH)_2$ + (D) $\longrightarrow$  I.3.

(J)

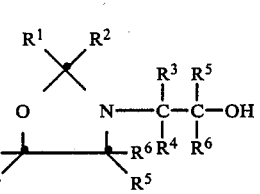

(K)

● (K) + $Q-(C_mH_{2m})Si(OR^9)_3 \longrightarrow$ (M)

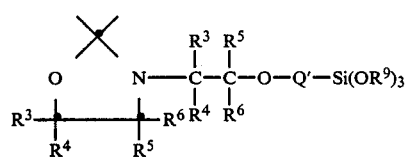

(N)

The first stage in this method is carried out as specified in German Offenlegungsschrift No. 2,446,438, while in the second stage a customary reaction with the free OH group in (K) is shown. Reactions which lead to the formation of esters or ethers are particularly suitable in this respect. The symbol Q indicates that this radical contains at least one substituent capable of such reactions. The carboxylic acid radical or anhydride, ester or (thio)urethane groups are particularly suitable in this regard. Q' indicates that the silane group is attached via an ester, ether, carbamate or thiocarbamate group. Examples of such types are shown in the formulae XI, XII, XIII, XIV, XV and XVI as constituents of the formula X. A large number of additional structures which are accessible by the same route are, of course, possible. However, since it is only essential for the invention that the radical Z should contain a silane group $-Si(OR^9)_3$ for this type of compound and it is not essential how this group is attached to the oxazolidine ring, a long list of bridge members would not contribute to an understanding of the present invention.

(I.4)

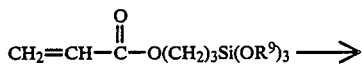

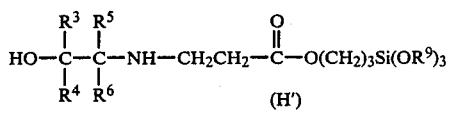

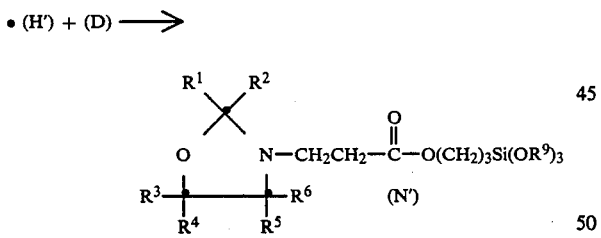

(N')

This method too is carried out by the known methods, to which reference has been made above.

II. Silane in one of the radicals R3, R4, R5 and R6

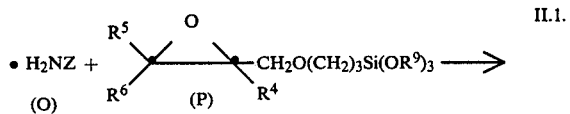

(II.1)

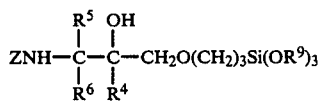

(R)

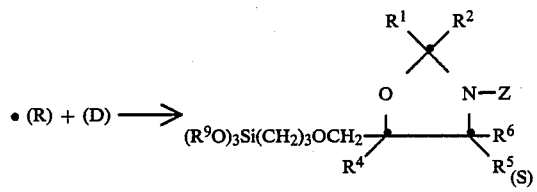

This method is carried out analogously to the instructions described in EP 96,768. The starting materials (O), (P) and (D) are commercially available or can be prepared by customary methods.

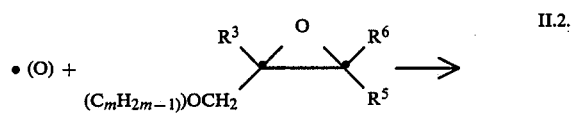

(II.2)

(T)

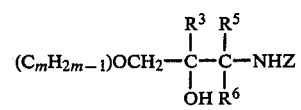

(U)

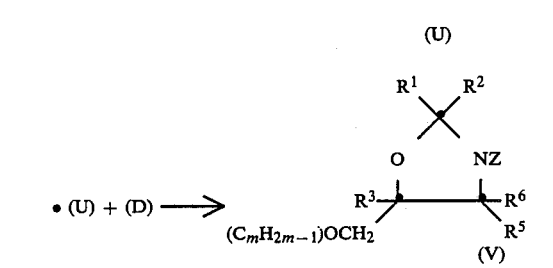

(V)

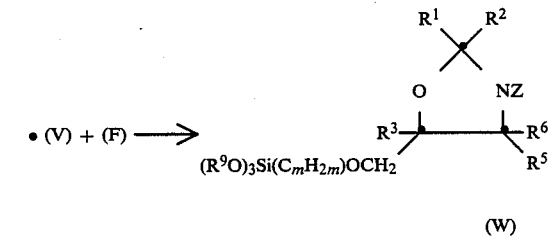

(W)

The procedure used in this method also is in accordance with known processes, such as are described, for instance, in EP-A 96,768.

II.3. Compounds of the formula I can also be obtained by means of the processes described in Chem. Pharm. Bulletin, 19, 2404 (1971).

II.4. Compounds of the formula I in which n is 2 are prepared analogously to processes II.1. and II.2., employing a diamine of the formula $H_2NZNH_2$ instead of a monoamine.

III. Silane in Z and in one of the radicals R3, R4, R4 or R6

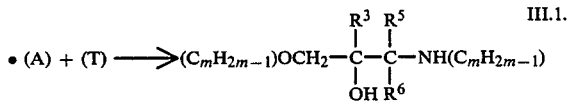

(III.1)

(Y)

-continued

• (Y) + (D) ⟶

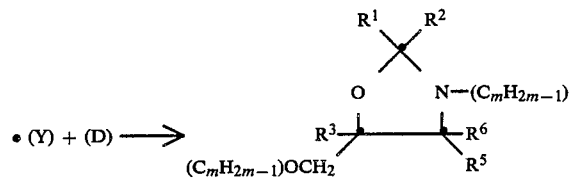

(AA)

• (AA) + (F) ⟶

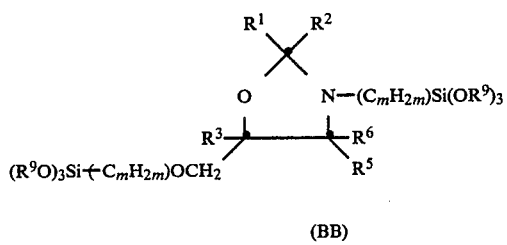

(BB)

This method corresponds to the method discussed under I.1. and II.2.

• (G) + (P) ⟶                             III.2.

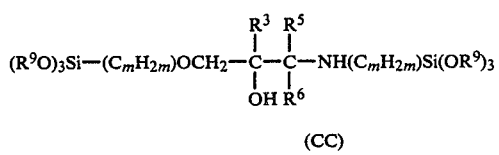

(CC)

• (CC) + (D) ⟶ (BB)

This method also corresponds to the processes described under I.1. and II.2. Compounds which are not embraced by these schemes are prepared analogously thereto, for example the compounds of the formula XVII analogously to method I.3.

In principle, the compounds according to the invention can be employed as adhesion promoters in various substrates. They are employed particularly effectively in moisture-curing epoxide resins and polyurethane resins which are used as adhesives, sealing compositions, paints or insulating materials. In the case of adhesives, the compounds according to the invention possess properties which enable them to be employed in two-component systems and, very particularly, in one-component systems. The use of the compounds according to the invention, especially as adhesion promoters incorporated in the substrates mentioned, makes it superfluous to pretreat, with a primer, the surfaces to be bonded. The bonding of windscreens and headlamps in automobile construction may be mentioned as examples of use. Compounds of the formula I in which n is 2 or polyfunctional compounds of the formula I in which n is 1 can, additionally, be employed as moisture-activated curing agents for the substrates mentioned.

If the moisture-curing resins are epoxide resins, they are preferably resins containing, directly attached to oxygen, nitrogen or sulfur atoms, groups of the formula

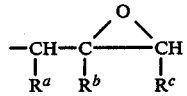

(XVIII)

in which either $R^a$ and $R^c$ are each a hydrogen atom, in which case $R^b$ is then a hydrogen atom or a methyl group, or $R^a$ and $R^c$ together are —CH$_2$CH$_2$—, in which case $R^b$ is then a hydrogen atom.

Examples of such resins which may be mentioned are polyglycidyl and poly-(β-methylglycidyl) esters which can be obtained by reacting a compound containing two or more carboxylic acid groups per molecule with epichlorohydrin, glycerol dichlorohydrin or β-methylepichlorohydrin in the presence of alkali. Polyglycidyl esters of this type can be derived from aliphatic polycarboxylic acids, for example oxalic acid, succinic acid, glutaric acid, adipic acid, pimelic acid, suberic acid, azelaic acid, sebacic acid or dimerized or trimerized linoleic acid, from cycloaliphatic polycarboxylic acids, such as tetrahydrophthalic acid, 4-methyltetrahydrophthalic acid, hexahydrophthalic acid and 4-methylhexahydrophthalic acid, and from aromatic polycarboxylic acids, such as phthalic acid, isophthalic acid and terephthalic acid.

Further examples are polyglycidyl and poly-(β-methylglycidyl) esters which are obtainable by reacting a compound containing at least two free alcoholic and-/or phenolic hydroxyl groups per molecule with the appropriate epichlorohydrin under alkaline conditions, or in the presence of an acid catalyst with subsequent treatment with alkali. These ethers can be prepared by means of poly-(epichlorohydrin) from acyclic alcohols, such as ethylene glycol, diethylene glycol and higher poly-(oxyethylene) glycols, propane-1,2-diol and poly-(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, pentaerythritol and sorbitol, from cycloaliphatic alcohols, such as resorcitol, quinitol, bis-(4-hydroxycyclohexyl)-methane, 2,2-bis-(4-hydroxycyclohexyl)-propane and 1,1-bis-(hydroxymethyl)-cyclohex-3-ene, and from alcohols containing aromatic nuclei, such as N,N-bis-(2-hydroxyethyl)-aniline and p,p'-bis-(2-hydroxyethylamino)-diphenylmethane.

They can also be prepared from mononuclear phenols, such as resorcinol and hydroquinone, and polynuclear phenols, such as bis-(4-hydroxyphenyl)-methane, 4,4-dihydroxybiphenyl, bis-(4-hydroxyphenyl) sulfone, 1,1,2,2-tetrakis-(4-hydroxyphenyl)-ethane, 2,2-bis-(4-hydroxyphenyl)-propane (otherwise known as bisphenol A) and 2,2-bis-(3,5-dibromo-4-hydroxyphenyl)-propane, and novolaks formed from aldehydes, such as formaldehyde, acetaldehyde, chloral and furfural, by means of phenols, such as phenol itself and phenols which are substituted in the ring by chlorine atoms or alkyl groups having in each case up to 9 carbon atoms, such as 4-chlorophenol, 2-methylphenol and 4-tert.-butylphenol.

Poly-(N-glycidyl) compounds embrace, for example, compounds obtained by dehydrochlorinating the reaction products of epichlorohydrin with amines containing at least two amino hydrogen atoms, such as aniline, n-butylamine, bis-(4-aminophenyl)-methane and bis-(4-methylaminophenyl)-methane, and also triglycidyl isocyanurate and N,N'-diglycidyl derivatives of cyclic alkyleneureas, such as ethyleneurea and 1,3-propyleneurea, and hydantoins, such as 5,5-dimethylhydantoin.

Examples of poly-(S-glycidyl) compounds are the di-S-glycidyl derivatives of dithiols, such as ethane-1,2-dithiol and bis-(4-mercaptomethylphenyl) ether.

Examples of epoxide resins containing groups of the formula XVIII in which $R^a$ and $R^b$ together are a —$CH_2CH_2$— group are bis-(2,3-epoxycyclopentyl) ether, 2,3-epoxycyclopentyl glycidyl ether and 1,2-bis-(2,3-epoxycyclopentyloxy)-ethane.

Epoxide resins in which the 1,2-epoxide groups are attached to heteroatoms of different types are also suitable, for example the N,N,O-triglycidyl derivative of 4-aminophenol, the glycidyl ether/glycidyl ester of salicylic acid or p-hydroxybenzoic acid, N-glycidyl-N'-(2-glycidyloxypropyl)-5,5-dimethylhydantoin and 2-glycidyloxy-1,3-bis-(5,5-dimethyl-1-glycidylhydantoin-3-yl)-propane.

If desired, mixtures of epoxide resins can be used.

Preferred epoxide resins are the polyglycidyl ethers, polyglycidyl esters and N,N'-diglycidylhydantoins. Particularly preferred resins are the polyglycidyl ethers of 2,2-bis-(4-hydroxyphenyl)-propane, of bis-(4-hydroxyphenyl)-methane or of a novolak which has been formed from formaldehyde and phenol or phenol substituted by a chlorine atom or an alkyl hydrocarbon group having 1 to 9 carbon atoms, and which has a content of 1,2-epoxide exceeding 0.5 equivalents/kg.

Examples of suitable curing agents for curing the resins mentioned at room temperature are aliphatic or cycloaliphatic ketimines or aldimines of primary amines, or enamines of secondary amines. Examples of suitable primary amines are aliphatic polyamines, including alkylenediamines, such as ethylenediamine, propane-1,2-diamine, propane-1,3-diamine, hexamethylenediamine or N,N-dimethylpropylene-1,3-diamine; and also diethyltriamine, triethylenetetramine or tetraethylenepentamine or ethanolamine. It is also possible to employ cycloaliphatic polyamines, for example bis-(aminocyclohexyl)-methane, bis-(4-amino-3-methylcyclohexyl)-methane or isophoronediamine. However, it is also possible to use polyaminoamides, for example the reaction products of aliphatic polyamines with dimerized or trimerized unsaturated fatty acids. Although the curing agents mentioned above are effective even at room temperature, curing can also be carried out at an accelerated rate at elevated temperatures.

The mixtures can also contain suitable plasticizing agents, such as dibutyl phthalate or dioctyl phthalate, inert diluents, such as tar or bitumen, or so-called reactive diluents, in particular monoepoxides, such as n-butyl glycidyl ether, isooctyl glycidyl ether, phenyl glycidyl ether, cresyl glycidyl ether, glycidyl esters of mixed, tertiary, aliphatic monocarboxylic acids, glycidyl acrylates and glycidyl methacrylates. They can also contain additives, such as fillers, reinforcing materials, colourants, flow control agents, fire-retarding materials and mould release agents.

Examples of suitable extenders, fillers and reinforcing materials are glass fibres, carbon fibres, small glass spheres, mica, quartz powder, calcium carbonate, cellulose, kaolin, wollastonite, colloidal silica of high specific surface, powdered polyvinyl chloride and powdered polyolefine hydrocarbons, such as polyethylene and polypropylene.

In the composition according to the invention, the resin/curing agent components mentioned above are employed in combination with silane-containing oxazolidines of the formula I, about 0.1–20% by weight, preferably 0.5–5% by weight, of the compound of the formula I being added, relative to the epoxy resin. In the case of polyfunctional oxazolidines of the formula I in which Z contains aldimine or ketimine groups, or in the case of polyoxazolidines in which n is 2, these oxazolidines can be employed as curing agents without additional curing agents being required. Care must be taken in this regard, however, that the molar ratio of liberated NH groups from the hydrolysed oxazolidine, in comparison with the epoxide content, does not become greater than 1.5 or less than 0.7, in order to ensure complete curing. Curing can be improved by heating or by adding accelerators.

If the substrates are moisture-curing polyurethanes, the latter contain, as the main constituent, polyfunctional isocyanates and/or polyurethane prepolymers. Both aromatic and aliphatic, monocyclic or polycyclic, polyfunctional isoyanate compounds are suitable in this case. Thus, in a first embodiment, toluidine diisocyanate or diphenylmethane diisocyanate can be employed as the aromatic isocyanate compound. Technical grade diphenylmethane diisocyanate having a content of diisocyanates of higher functionality and a functionality of isocyanate groups greater than 2 is particularly suitable. A futher suitable aliphatic diisocyanate is xylylene diisocyanate. In addition, it is possible to employ a large number of aliphatic isocyanates having a functionality of 2 or more. Examples of these are isophorone dissocyanate and dicyclohexylmethane diisocyanate, as cyclic aliphatic diisocyanates. Further examples are aliphatic, linear diisocyanates, such as are obtained by reacting diamines with phosgene, for example tetramethylene diisocyanate or hexamethylene diisocyanate.

In a preferred embodiment of the invention, polyurethane prepolymers are employed instead of the polyfunctional isocyanate compounds. Prepolymers are to be understood here as meaning the adducts of an excess of polyfunctional isocyanates reacted with polyfunctional alcohols, for instance the reaction products of one of the aromatic or aliphatic diisocyanates mentioned above with ethylene glycol, propylene glycol, glycerol, trimethylolpropane or pentaerythritol. Reaction products of diisocyanates with polyether-polyols, for example polyether-polyols based on polyethylene oxide or based on polypropylene oxide, can be used as prepolymers. Polyurethane prepolymers based on polyether-polyols having molecular weights between 200 and 10,000, in particular 500 and 3000, are preferred. A large number of polyether-polyols of this type are known to those skilled in the art of polyurethanes; they are available from numerous manufacturers and are characterized by their molecular weight (number average), which can be calculated from end group determinations. Further suitable polyether-polyols are polyether-polyols based on polytetrahydrofuran.

It is also possible to employ polyester-polyols instead of polyether-polyols. Suitable polyester-polyols are reaction products of polyfunctional acids with polyfunctional alcohols, for example polyesters based on aliphatic and/or aromatic dicarboxylic acids and polyfunctional alcohols having a functionality of 2–4. Thus it is possible to employ polyesters formed from adipic acid, sebacic acid, phthalic acid, hydrophthalic acid and/or trimellitic acid, on the one hand, and from ethylene glycol, propylene glycol, neopentyl-glycol, hexane glycol, glycerol and/or trimethylolpropane, on the other hand, Polyester-polyols having a molecular weight (number average) between 500 and 5000, in particular between 600 and 2000, are particularly suitable. Further suitable polyester-polyols are the reaction products of caprolactone with alcohols having a functionality of 2-4, for example the addition product of 1-5 mol of caprolactone with 1 mol of ethylene glycol, propylene glycol, glycerol and/or trimethylolpropane.

A further suitable class of polyfunctional alcohols is formed by polybutadienols. These are oligomers based on butadiene, containing OH groups as end groups. Products within the molecular weight range of 200-4000, in particular 500-3000, are suitable in this case.

In the preparation of the polyurethane prepolymers, the ratio of OH groups in the alcohol component to isocyanate groups is an important factor. In general, this is between 1:2 and 1:10. In this respect, low-viscosity polyurethane prepolymers are more likely to be obtained with a higher excess of isocyanate, while high-viscosity preparations, in most cases preparations which are only still trowelable, are obtained with a low excess of isocyanate.

It is known to those skilled in the art of polyurethanes that the crosslinking density and hence the hardness and brittleness of the polyurethanes increases with the functionality of the isocyanate component or of the polyol. Reference should be made in this regard to the general technical literature, for example to the monograph by Saunders and Frisch "Polyurethanes, Chemistry and Technology", volume XVI in the series "High Polymers", Interscience Publishers New York-London, part I (1962) and part II (1964).

The polyurethane preparations according to the invention can also contain various auxiliaries. For example, fillers can be used here. Suitable fillers are inorganic compounds which are non-reactive towards isocyanates, for example chalk or powdered lime, precipitated and/or pyrogenic silicas, zeolites, bentonites, ground minerals and other inorganic fillers which are known to the specialist active in this field, in particular short-staple fibres and other materials. For some applications fillers which impart thixotropy to the preparations are preferred, for example swellable plastics, in particular PVC.

Apart from the compounds mentioned, the polyurethane preparations according to the invention can also contain further auxiliaries, for example solvents. Solvents which do not for their part react with isocyanate groups are suitable, for example halogenated hydrocarbons, esters, ketones, aromatic hydrocarbons and others. It is also possible to incorporate plasticizers, fire-retarding agents, retarders, dyestuffs and anti-ageing agents, such as are known in polyurethane adhesives and sealing compositions.

For some applications it is desirable to add foam stabilizers to the polyurethane preparations according to the invention. So-called silico-surfactants can be used as foam stabilizers. These are block copolymers composed of a polysiloxane block and one or more polyoxyethylene and/or polyoxypropylene blocks. The polyurethane preparations according to the invention can also contain fire-retarding and plasticizing additives. Compounds containing phosphorus and/or halogen atoms are customary, such as tricresyl phosphate, diphenyl cresyl phosphate, tris-2-chloroethyl phosphate, tris-2-chloropropyl phosphate and tris-2,3-dibromopropyl phosphate. In addition, it is possible to use fire-retarding agents, for example chloroparaffins, halogen phosphides, ammonium phosphate and resins containing halogen and phosphorus. Plasticizers are important as further additives for some applications. Examples of plasticizers suitable for this purpose are esters of phthalic acid or esters of long-chain dicarboxylic acids, for example sebacic or azelaic acid esters. So-called epoxide plasticizers, for example epoxidized fatty acid derivatives, can also be employed here.

Further possible additives are basic accelerators. These should not be used if carboxylic anhydrides are employed as accelerators. Examples of basic accelerators are tertiary bases, such as bis-(N,N'-dimethylamino)-diethyl ether, dimethylaminocyclohexane, N,N-dimethylbenzylamine, N-methylmorpholine and the reaction products of dialkyl-($\beta$-hydroxyethyl)-amines with monoisocyanates and esterification products of dialkyl-($\beta$-hydroxyethyl)-amines and dicarboxylic acids. Another important accelerator is 1,4-diaminobicyclo(2.2.2)octane. It is also possible to use non-basic substances as accelerators. Mention may be made here of metal compounds, for example iron pentacarbonyl, nickel tetracarbonyl, iron acetylacetonate and tin-(II) 2-ethylhexoate, dibutyltin dilaurate or molybdenum glycollate.

In general, the compounds of the formula I are added to polyurethane prepolymers in amounts of 0.1-20% by weight, preferably 0.5-5% by weight, relative to the prepolymer.

If the compounds of the formula I are employed as curing agents, the molar ratio of liberated >NH groups to free isocyanate groups in the prepolymer should suitably be 0.5 to 1.5:1, preferably 0.9 to 1.1:1.

EXAMPLE 1

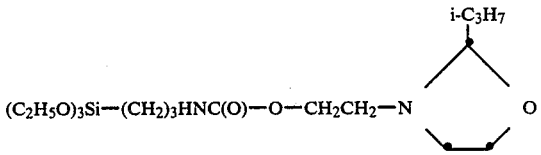

32.1 g (0.202 mol) of n-hydroxyethyl-2-isopropyl-(1,3)-oxazolidine (boiling point 70° C./0.1, prepared from isobutyraldehyde and diethanolamine) are added dropwise at 60° C. to a mixture of 50 g (2.202 mol) of isocyanatopropyltriethoxysilane and 0.1 ml of dibutyltin dilaurate. After the slightly exothermic reaction has subsided, the mixture is stirred for 12 hours at 60° C. 79 g (95% of theory) of a liquid having the following analytical data are isolated:

Viscosity $\eta_{25°\,C.}$: 50 mPas
Refractive index $n_D^{25}$: 1.452
Titration: 2: 36 mol of NH/kg (calculated 2.46)
Elementary analysis:

|     | Found | Calculated |
| --- | ----- | ---------- |
| % C | 53.00 | 53.17 |
| % H | 9.19  | 9.42 |
| % N | 7.01  | 6.89 |

EXAMPLE 2

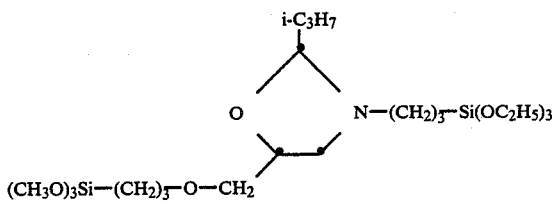

236 g (1 mol) of glycidyloxypropyltrimethoxysilane are added dropwise at 40° C. to a mixture of 222 g (1 mol) of aminopropyltriethoxysilane in 1 l of anhydrous ethanol in the presence of 10 mg of p-toluenesulfonic acid monohydrate. After the slightly exothermic reaction has subsided, the mixture is kept at reflux temperature for 12 hours. After the ethanol has been removed by distillation in a water pump vacuum, 1 l of toluene, 150 g of isobutyraldehyde and 200 mg of p-toluenesulfonic acid are added, and the mixture is stirred for 1 hour at 60° C. and boiled overnight under a water separator in order to remove the resulting water azeotropically. The volatile components are then removed on a rotary evaporator under a water pump vacuum, and the residue is dried for 1 hour at 60° C./0.133 mbar. 457 g (89% of theory) of a liquid having the following analytical data are isolated:

Viscosity $\eta_{25°\ C.}$ = 150 mPas
Refractive index $n_D^{25}$ = 1.452
Titration: 2.0 mol of NH/kg (calculated 1.96)

|     | Found | Calculated |
| --- | --- | --- |
| % C | 51.50 | 51.65 |
| % H | 9.40 | 9.65 |
| % N | 2.70 | 2.74 |

EXAMPLE 3

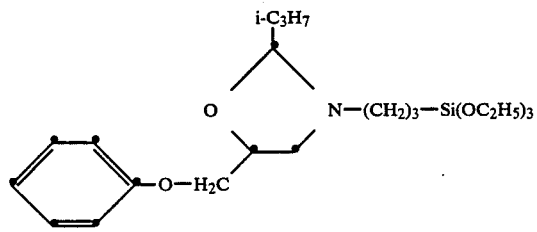

150 g (1 mol) of phenyl glycidyl ether are added dropwise at 30° C. to a mixture of 22 g (1 mol) of aminopropyltriethoxysilane and 1 l of anhydrous ethanol in the presence of 10 mg of p-toluenesulfonic acid monohydrate, and the mixture is kept at reflux temperature for 12 hours. After the ethanol has been removed under a water pump vacuum, 500 ml of toluene, 100 g of isobutyraldehyde and 100 mg of p-toluenesulfonic acid monohydrate are added at room temperature, and the mixture is stirred for 1 hour at 60° C. and boiled overnight under a water separator in order to remove, by azeotropic distillation, the water which has been formed. All the volatile constituents are then removed on a rotary evaporator, first at 60° C./water pump vacuum and then for 1 hour at 60° C. and 0.133 mbar. A liquid having the following analytical data is isolated:

Viscosity $\eta_{25°\ C.}$: 200 mPas
Refractive index $n_D^{25}$: 1.492
Titration: 2.27 mol of NH/kg (calculated 2.35)
Elementary analysis:

|     | Found | Calculated |
| --- | --- | --- |
| % C | 61.62 | 62.08 |
| % H | 8.73 | 9.24 |
| % N | 3.67 | 3.29 |

EXAMPLE 4

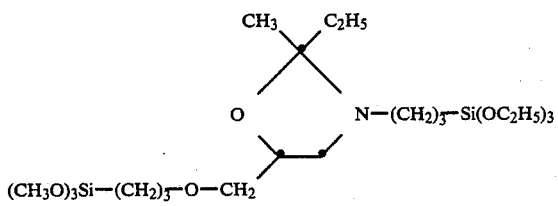

146 g (0.66 mol) of aminopropyltriethoxysilane are added, under nitrogen, to a mixture of 155 g (0.66 mol) of glycidyloxypropyltrimethoxysilane in 500 ml of anhydrous toluene at 60° C. and in the course of 40 minutes, and the mixture is stirred for 3 hours at 80° C. and allowed to cool to room temperature. 300 g of ethyl methyl ketone and a further 500 g of toluene are then added, the mixture is stirred for 1 hour at room temperature, 100 mg of p-toluenesulfonic acid monohydrate are added and the mixture is boiled for 12 hours at reflux temperature under a water separator. The toluene is then removed in vacuo at 60° C. and the residue is filtered and dried for 1 hour at 60° C./0.532 mbar. Yield: 281 g (86% of theory) of a liquid having the following properties:

Viscosity $\eta_{25°\ C.}$: <50 mPas
Refractive index $n_D^{25}$: 1.442
Titration: 1.98 mol of NH/kg (calculated 1.96)
Elementary analysis:

|     | Found | Calculated |
| --- | --- | --- |
| % C | 51.98 | 51.65 |
| % H | 9.37 | 9.65 |
| % N | 2.81 | 2.74 |

EXAMPLE 5

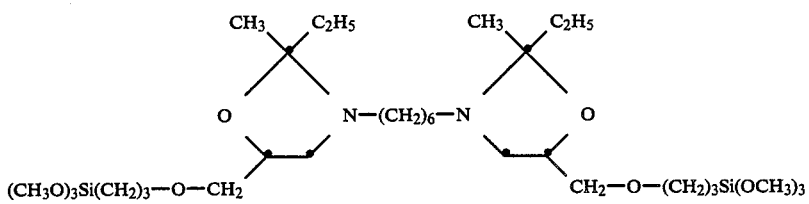

A mixture of 58 g (0.5 mol) of 1,6-diaminohexane and 500 ml of toluene is initially taken, under nitrogen, and 236 g (1.0 mol) of 3-glycidyloxypropyltrimethoxysilane are added at 60° C., in the course of 30 minutes, and the mixture is stirred for 2 hours at 80° C. A further 500 ml of toluene are then added, the mixture is allowed to cool to 30° C., 300 g of ethyl methyl ketone are added and the mixture is stirred at room temperature for 1 hour. After 100 mg of p-toluenesulfonic acid monohydrate have been added, the mixture is boiled at reflux temperature under a water separator for 12 hours. The solvent is removed in vacuo at 60° C. and the liquid is filtered and freed from residual solvent at 60° C./0.532 mbar. 281 g (84% of theory) of a liquid having the following properties are isolated:

Viscosity $\eta_{25°\,C.}$: 80 mPas
Refractive index $n_D^{25}$: 1.457
Titration: 3.05 mol of NH/kg (calculated 2.87)
Elementary analysis:

|      | Found | Calculated |
|------|-------|------------|
| % C  | 54.78 | 55.15      |
| % H  | 9.51  | 9.84       |
| % N  | 4.39  | 4.02       |

EXAMPLE 6

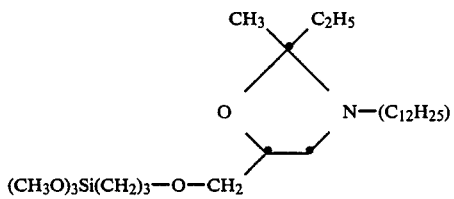

185 g (1 mol) of dodecylamine in 500 ml of toluene are initially taken, under nitrogen, and 236 g (1 mol) of glycidyloxypropyltrimethoxysilane are added at 80° C. in the course of 2 hours, and the mixture is then stirred for 2 hours at 80° C. 1 l of toluene is then added, the mixture is allowed to cool and 300 g of ethyl methyl ketone are added. After 1 hour, 100 mg of p-toluenesulfonic acid monohydrate are added and the mixture is boiled at reflux temperature under a water separator for 12 hours. The solvent is then removed in vacuo at 60° C. and the slightly yellowish liquid is filtered and freed from residual solvent at 60° C./0.532 mbar for one hour. Yield 450 g (95% of theory) of a liquid having the following analytical data:

Viscosity $\eta_{25°}$ C.: <50 mPas
Refractive index $n_D^{25}$: 1.458
Titration: 1.88 mol of NH/kg (calculated 2.10)
Elementary analysis:

|      | Found | Calculated |
|------|-------|------------|
| % C  | 67.20 | 63.12      |
| % H  | 10.20 | 11.23      |
| % N  | 2.82  | 2.94       |

EXAMPLE 7

221 g (1 mol) of aminopropyltriethoxysilane are added dropwise, under nitrogen and at room temperature, to 150 g (1 mol) of phenyl glycidyl ether in 1 l of toluene in the course of 30 minutes. The mixture is stirred at room temperature for 2 hours and is then heated at 80° C. for 4 hours. 200 mg of p-toluenesulfonic acid monohydrate are then added, the mixture is cooled to below 50° C., ethyl methyl ketone is added and the mixture is boiled at reflux temperature under a water separator for 12 hours. The solvent is then removed in vacup at 60° C. and the product is filtered and dried for 1 hour at 60° C./0.532 mbar. Yield: 370.4 g (87% of theory) of a liquid having the following analytical data:

Viscosity $\eta_{25°}$ C.: 220 mPas
Refractive index $n_D^{25}$: 1.490
Titration: 2.38 mol of NH/kg (calculated 2.35)
Elementary analysis:

|      | Found | Calculated |
|------|-------|------------|
| % C  | 60.84 | 62.09      |
| % H  | 8.96  | 9.23       |
| % N  | 3.67  | 3.29       |

EXAMPLE 8

(A) Synthesis of prepolymer:

A mixture of 177 g of anhydrous polypropylene glycol, MW 2000 (Desmophen ® 1900 U), 0.9 g of trimethylolpropane and 0.1 ml of dibutyltin dilaurate are added, under nitrogen and at 80° C., to methylenediphenyl diisocyanate (Isonate ® 125M), and the mixture is stirred at 80° C. for 2 hours. A prepolymer having an isocyanate content of 3.7% by weight is formed.

(B) Bonding steel to glass and adhesion to glass:

The adhesion promoters described above are added to the prepolymer mixture A, and this moisture-curing one-component polyurethane is used to bond steel test specimens (17×2.5 cm) which have an overlap of 1.25×2.5 cm and hold a glass slide (3.8×2.5 cm) in the form of a sandwich. Additionally, the adhesive is applied to a sheet of glass which, after a curing time of two weeks, is stored in water at room temperature for 4 weeks. The results are collected in the following table:

| Mixture No. | Adhesion promoter according to Example No. (g) | Steel/glass tensile shear strength (N/mm²) | Type of fracture * | Adhesion to glass ** |
|---|---|---|---|---|
| (Prepolymer) | — — | 0.6 | A | — |
| | 4 (9) | 1.4 | K | + |
| | 5 (9) | 1.5 | K | + |
| | 6 (9) | 1.2 | K | + |

*Type of fracture A = adhesive fracture, K = cohesive fracture
**Adhesion to glass: - represents polyurethane which can already be removed from the glass surface after a short time, whereas + indicates that it could not be removed manually

EXAMPLE 9

A prepolymer is prepared by adding 77.67 g of anhydrous polypropylene glycol, MW 2000 (Desmophen® 1900 U), at 70° C. and in the course of one hour, to 21.9 g of methylenediphenyl diisocyanate containing 0.04 ml of dibutyltin dilaurate. After 0.39 g of trimethylolpropane have been added, the mixture is stirred at 70° C. for a further hour, and a prepolymer containing 3.7% by weight of free isocyanate is obtained. Adhesion promoter is added to this prepolymer and the one-component polyurethane modified in this way is applied to various materials. The arrangements are collated in the table below, in which + indicates, as a quantitative measure of the adhesion, that it was not possible to separate the cured polyurethane layer manually from the substrate.

| Adhesion promoter according to Example No. | % by weight | ABS | PA | PC | PP | PVC | SMC | Steel | Al | G | SG |
|---|---|---|---|---|---|---|---|---|---|---|---|
| (prepolymer) | — | — | — | + | — | — | + | — | — | — | — |
| 4 | (4.3) | + | + | + | — | + | + | + | + | + | + |
| 6 | (4.1) | + | + | + | — | + | + | + | — | + | + |

ABS: acrylonitrile/butadiene/styrene
PA: polyamide
PC: polycarbonate
PP: polypropylene
PVC: polyvinyl chloride
SMC: glass-reinforced polyester
G: glass
SG: safety glass

What is claimed is:
1. A moisture-curing epoxide or polyurethane resin containing at least one compound of formula I

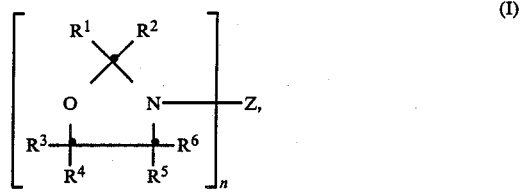

in which $R^1$ is hydrogen, $C_1$-$C_{12}$-alkyl, $C_5$-$C_7$-cycloalkyl, phenyl or benzyl and $R^2$ is hydrogen or $C_1$-$C_4$-alkyl, or $R^1$ and $R^2$, together with the C atom to which they are attached, form a 5-membered or 6-membered ring, and $R^3$, $R^4$, $R^5$ and $R^6$ are identical or different and are hydrogen, $C_1$-$C_{12}$-alkyl, phenyl which is unsubstituted or monosubstituted to trisubstituted by $C_1$-$C_4$-alkyl, halogen or $C_1$-$C_4$-alkoxy, or is a group of the formula —$CH_2OR^7$ (II) in which $R^7$ is $C_1$-$C_{12}$-alkyl, phenyl which is unsubstituted or monosubstituted to trisubstituted by $C_1$-$C_4$-alkyl, halogen or $C_1$-$C_4$-alkoxy, or is —C(O)—$R^8$, and $R^8$ is $C_1$-$C_{12}$-alkyl, and additionally not more than two of the radicals $R^3$, $R^4$, $R^5$ and $R^6$ are one or two groups of the formula —$CH_2CH_2Si(OR^9)_3$ (III), —$CH_2OC(O)CH_2CH_2Si(OR^9)_3$ (IV), —$CH_2O(C_mH_{2m})Si(OR^9)_3$ (V) or

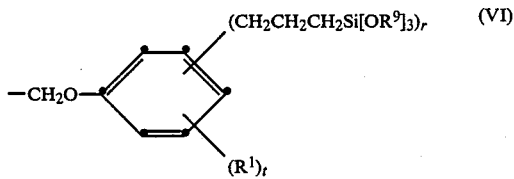

in which $R^9$ is $C_1$-$C_4$-alkyl or phenyl and m is a number from 1 to 8 and r is a number 1 or 2 and t is 0, 1 or 2 and $R^1$ is as defined above, or in addition, compounds of the formula I in which $R^4$ and $R^5$ together form a group of the formula

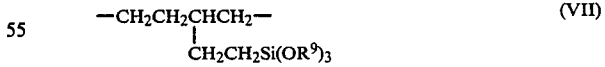

in which $R^9$ is as defined above and $R^3$ and $R^6$ in this case are hydrogen, n is 1 or 2, and, when n is 1, Z is the organic radical of a primary amine $ZNH_2$ without the $NH_2$ group, and, when n is 2, Z is the divalent organic radical of a diprimary diamine $NH_2ZNH_2$ without the two $NH_2$ groups; subject to the proviso that the compound of formula I contains one to three—$Si(OR^9)_3$ groups.
2. A polyurethane resin according to claim 1.
3. A resin according to claim 1, containing 0.1–20% by weight of a compound of the formula I.

* * * * *